(12) United States Patent
Grasso et al.

(10) Patent No.: US 11,109,594 B2
(45) Date of Patent: Sep. 7, 2021

(54) STORAGE STABLE AZADIRACHTIN FORMULATIONS AND METHODS OF MAKING AND USING THE SAME

(71) Applicant: GOWAN COMPANY, L.L.C., Yuma, AZ (US)

(72) Inventors: Charles Paul Grasso, Yuma, AZ (US); Rene Garcia Cochran, Yuma, AZ (US)

(73) Assignee: GOWAN COMPANY, L.L.C., Yuma, AZ (US)

(*) Notice: Subject to any disclaimer, the term of this patent is extended or adjusted under 35 U.S.C. 154(b) by 0 days.

(21) Appl. No.: 16/326,125

(22) PCT Filed: Aug. 16, 2017

(86) PCT No.: PCT/US2017/047201
§ 371 (c)(1),
(2) Date: Feb. 15, 2019

(87) PCT Pub. No.: WO2018/035254
PCT Pub. Date: Feb. 22, 2018

(65) Prior Publication Data
US 2019/0174761 A1    Jun. 13, 2019

Related U.S. Application Data

(60) Provisional application No. 62/376,240, filed on Aug. 17, 2016.

(51) Int. Cl.
*A01N 43/90* (2006.01)
*A61K 36/58* (2006.01)
(Continued)

(52) U.S. Cl.
CPC ............ *A01N 43/90* (2013.01); *A01N 25/04* (2013.01); *A01N 25/30* (2013.01); *A61K 36/58* (2013.01); *A01N 65/26* (2013.01)

(58) Field of Classification Search
None
See application file for complete search history.

(56) References Cited

U.S. PATENT DOCUMENTS 5,001,146 A * 3/1991 Carter .................... A01N 65/26
514/453
5,104,647 A * 4/1992 Policello ................ A01N 25/30
424/407

(Continued)

FOREIGN PATENT DOCUMENTS

WO    WO-2006053577 A1 *  5/2006  ............ A61Q 19/00
WO    WO 2008/057703 A2    5/2008
(Continued)

OTHER PUBLICATIONS

Tipping et al. (Efficacy of Silwet L-77 Against Several Arthropod Pests of Table Grape, Entomological Society of America, 2003) (Year: 2003).*

(Continued)

*Primary Examiner* — Melissa S Mercier
(74) *Attorney, Agent, or Firm* — Arent Fox LLP

(57) ABSTRACT

Formulations comprising compounds obtainable from a neem extract and/or biomass and at least one water-soluble organosilicone surfactant, and methods of making and using such formulations are provided.

25 Claims, 3 Drawing Sheets

(51) Int. Cl.
*A01N 25/04* (2006.01)
*A01N 25/30* (2006.01)
*A01N 65/26* (2009.01)

(56) References Cited

U.S. PATENT DOCUMENTS

| | | | |
|---|---|---|---|
| 5,352,697 A * | 10/1994 | Butler | A01N 43/90 514/468 |
| 5,356,628 A | 10/1994 | Locke et al. | |
| 5,405,612 A | 4/1995 | Locke et al. | |
| 6,277,416 B1 | 8/2001 | Harkrader et al. | |
| 6,811,790 B1 | 11/2004 | Damaria et al. | |
| 2007/0020304 A1 | 1/2007 | Tamarkin et al. | |
| 2009/0170704 A1 | 7/2009 | Kober et al. | |

FOREIGN PATENT DOCUMENTS

| | | | | |
|---|---|---|---|---|
| WO | 2016053577 A1 | 4/2016 | | |
| WO | WO-2016053577 A1 * | 4/2016 | ............ | A01N 25/10 |
| WO | 2016090314 A1 | 6/2016 | | |

OTHER PUBLICATIONS

Shah et al. (Comparative role of neem seed extract, moringa leaf extract and imidacloprid in the management of wheat aphids in relation to yield losses in Pakistan, 2017, PLos One 12(9)). (Year: 2017).*

International Search Report as cited in International Application No. PCT/US2017/047201, dated Oct. 30, 2017.

Rajashekar, Y., et al., "Botanicals as Grain Protectants ", Psyche, Jun. 14, 2012, vol. 2012, Article ID 646740, pp. 1-13.

Knoche, M., "Organosilicone surfactant performance in agricultural spray application: a review", Weed Research, Jun. 1994, vol. 34, pp. 221-239.

Extended European Search Report received in European Patent Application No. 17842073, dated Feb. 26, 2020.

* cited by examiner

STORAGE STABLE AZADIRACHTIN FORMULATIONS AND METHODS OF MAKING AND USING THE SAME

CROSS-REFERENCE TO RELATED APPLICATIONS

This application is a 35 U.S.C. 371 National Phase of PCT Application No. PCT/US2017/047201, filed on Aug. 16, 2017, which claims priority to US Provisional Application No. 62/376,240, filed Aug. 17, 2016, the disclosure of which is hereby incorporated by reference in its entirety.

FIELD OF INVENTION

Formulations comprising compounds obtainable from a neem extract and/or biomass and at least one water-soluble organosilicone surfactant, and methods of making and using such formulations are provided.

BACKGROUND OF INVENTION

Extracts from the neem tree, such as the leaves and seeds, are known to possess insecticidal activity. For example, azadirachtin is a well-known pesticidal agent derived from seeds of the neem fruit. There are many structurally related forms of azadirachtin, including azadirachtin A and B.

Azadirachtin formulations are known to degrade in storage, and researchers have long sought a solution for developing improved azadirachtin formulation. These efforts, and general background information on azadirachtin, are detailed in various patents and publications, such as U.S. Pat. No. 6,811,790 and WO 2008/057703, each of which are hereby incorporated by reference in their entirety.

U.S. Pat. No. 6,811,790 discloses a pesticide formulation that comprises vegetable oil (1-60% by weight), sorbitan trioleate surfactant (20-55% by weight) and a neem seed extract containing azadirachtin (1 to 5% by weight). The patent reports that, in an accelerated storage test, a significant amount of azadirachtin A is degraded in 14 days at 54° C. For example, the degradation of azadirachtin A in the Formulations I-IV is 68.25%, 59.60%, 35.35%, and 27.77%, respectfully.

WO 2008/057703 discloses a pesticide formulation that comprises azadirachtin (about 0.01% to 3% by weight), a pyrethin or pyrethroid (about 0.01 to about 10% by weight), and a heterocyclic or aromatic solvent (about 70% to about 90% by weight). The application reports that the pyrethin or pyrethroid prevents decomposition of the azadirachtin, and asserts that the formulation is shelf-stable because at least about 90% of the azadirachtin originally present remains after an accelerated aging test of 30 days at 40° C. in a sealed container.

SUMMARY OF VARIOUS EMBODIMENTS OF THE DISCLOSURE

The disclosure provides compositions that generally comprise compounds obtainable from a neem extract and/or biomass (e.g., azadirachtin) and a water-soluble organosilicone surfactant, and methods of using the same. The compositions are shelf-stable, liquid concentrates that do not contain a protic solvent. The compositions can be diluted by water to form a pesticide formulation and applied to an environment, such as plants and trees. The resulting pesticide formulation may comprise multiple components, such as a solution, micro-emulsion, and/or a nano-suspension. Methods of making the compositions and using the compositions are also provided.

DETAILED DESCRIPTION OF VARIOUS EMBODIMENTS

Figure 1A:
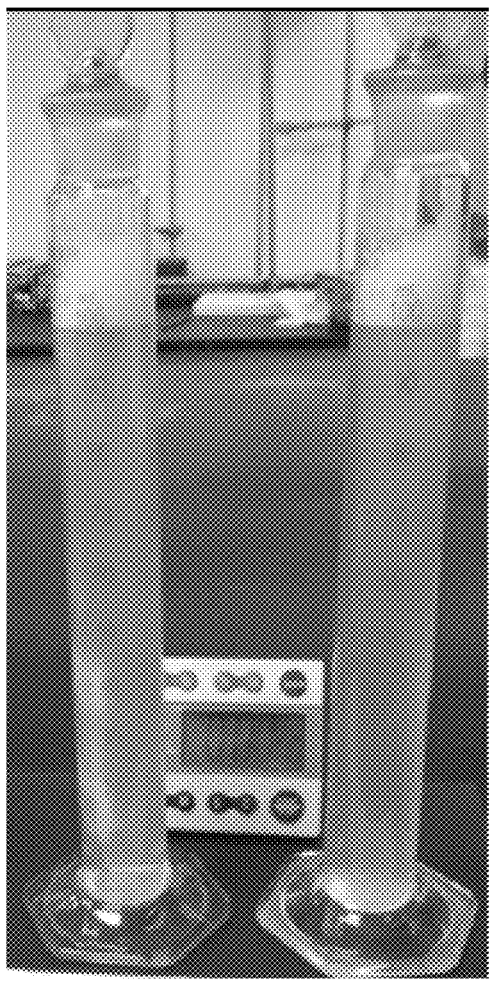
FIGS. 1A, 1B, and 1C show graduated cylinders of microemulsions and nano-suspensions comprising azadirachtin with a 3.6% w/w (left side) and 7.2% w/w (right side), and a water-soluble organosilicone surfactant, after 0 hours (FIG. 1A), ~2 hours (FIG. 1B), and ~22 hours (FIG. 1C) of preparing the formulations. Neither precipitation nor layering was observed at ~22 hours.

The disclosure provides pesticidal compositions and methods of making and using pesticidal compositions. The compositions generally comprise a neem extract and/or biomass comprising, for example, azadirachtin and a water-soluble organosilicone surfactant, but lack a protic solvent. The compositions may be diluted and applied (e.g., sprayed) to any desired environment, such as a lawn or crop field. The compositions may be used for organically approved and conventional agronomic uses.

Surprisingly, the inventors have obtained compositions comprising azadirachtin that are shelf-stable and have increased concentration of azadirachtin compared to prior art formulations. For example, the inventors have found that at least 90% of azadirachtin remains after accelerated storage of 14 days at 54° C. in a sealed container. The compositions are typically clear concentrates that, upon dilution with water, form solutions, micro-emulsions, and/or nano-suspensions. As a result, the compositions provide a highly concentrated, stable, and active pesticidal agent.

The compositions comprise compounds obtainable from a neem extract and/or biomass (e.g., azadirachtin, terpenoids, limonoids, alkaloids and/or other secondary metabolites). The azadirachtin is preferably at least azadirachtin A and/or B. Other forms of azadirachtin can be used alternatively, or in combination with the preferred azadirachtins. For example, other structurally related azadirachtins can be used such as C, D, E, F, G, H, I, J, and/or K, and the like. For purposes of this disclosure, azadirachtin includes one or more types of azadirachtins. In other aspects, the compositions comprise one or more of terpenoids, limonoids, alkaloids and other secondary metabolites obtained from a neem extract and/or biomass without azadirachtin.

The amount of azadirachtin present in the compositions described herein can be any amount with effective insecticidal activity, such as, but not limited to, an amount effective to reduce and/or eliminate insecticidal damage to trees and/or crops. In one aspect, the amount of azadirachtin present is from 0.1% weight to 30.0% weight; 0.1% weight to 10.0% weight; 3.5% weight to 30.0%, 3.5% weight to 10.0% weight, 3.5% weight to 8.0% weight based on the weight of the composition. In other aspects, the amount of azadirachtin present is from 0.1%, 0.5%, 1%, 1.2%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 11%, 12%, 13%, 14%, 15%, 16%, 17%, 18%, 19%, 20%, 21%, 22%, 23%, 24%, 25%, 26%, 27%, 28%, 29%, 30%, or more weight based on the weight of the composition. In other aspects, the amount of azadirachtin present is any range based on a combination of these percentages recited in the preceding sentence (e.g., 3.0%-8.0%, 3.5%-7.5%, 3%-4%, 7%-8%, etc. weight based on the weight of the composition). In particular aspects, the amount of azadirachtin present is 3.6% or 7.2% weight based on the weight of the composition.

In other aspects, the amount of one or more of terpenoids, limonoids, alkaloids and other secondary metabolites, without azadirachtin, present in the compositions described herein can be any amount with effective insecticidal activity, such as, but not limited to, an amount effective to reduce and/or eliminate insecticidal damage to trees and/or crops.

The azadirachtin, terpenoids, limonoids, alkaloids and other secondary metabolites may be recovered from the seeds of a neem tree by crushing the seeds and then extracting the compounds from the crushed seeds with water. The extracting of azadirachtin, terpenoids, limonoids, alkaloids and other secondary metabolites from the water is accomplished using a non-aqueous solvent which is not miscible with water and has a high solubility of azadirachtin than water, or by using a surfactant having a turbidity temperature between 20° and 80° C. The concentrated azadirachtin is then recovered from the second extracting solution. The azadirachtin containing solution is then concentrated to produce an azadirachtin concentrate which is added to a liquid hydrocarbon, thus forming an azadirachtin precipitate that is then recovered for use in pesticide formulations. The azadirachtin can also be recovered by the techniques set forth in U.S. Pat. Nos. 4,556,562 and 5,124,349, which are hereby incorporated by reference, as well as other conventional methods.

The azadirachtin may be obtained from a commercial technical product derived from neem. Such commercial products include azadirachtin and other metabolites, such as terpenoids, limonoids, alkaloids and other secondary metabolites. For example, azadirachtin may be present in an amount of 30% by weight of such a product. The disclosure contemplates using such technical products as the source of azadirachtin and thus the concentration of the azadirachtin in the commercial product must be taken into account when determining the amount of azadirachtin in the compositions described herein. For example, a composition described herein may contain 6% azadirachtin by weight based on the following calculation:

| Component | (w/w)% in Formula |
|---|---|
| Water-soluble organosilicone surfactant | 80% |
| Technical Product (30% azadirachtin) | 20% |
| | 100% |

The concentration of one or more of terpenoids, limonoids, alkaloids and other secondary metabolites in the compositions described herein can likewise be determined by using the concentration of these compounds in a commercial technical product derived from neem.

In other aspects, one or more of azadirachtin, terpenoids, limonoids, alkaloids and other secondary metabolites obtainable from a neem extract or biomass may be synthesized and/or bioengineered. It will be appreciated that natural extracts are typically obtained as crude extracts that may have limited concentration(s) of compounds having pesticidal activity. The concentration of such compounds may be increased via purification. Alternatively, the concentration of these compounds may be increased by independently synthesizing or bio-engineering these compounds. The only limitation would be the solubility of the chemical compound in the organosilicone surfactant.

The composition comprises a water-soluble organosilicone surfactant or mixtures thereof. In one aspect, the water-soluble organosilicone surfactant is a water-soluble, non-ionic polysiloxane. The organo groups of the polyorganosiloxane comprise alkyl, aryl and/or polymeric groups. The polyorganosiloxane may be linear, cyclic (like trisiloxanes), branched or crosslinked. In one aspect, the organo groups of the polyorganosiloxane comprise polymeric groups in addition to alkyl and/or aryl groups. Examples of alkyl groups are $C_1$-$C_{12}$ alkyl and methyl. Examples of aryl groups are phenyl or substituted phenyl groups. Polymeric groups include polyether, e.g., polyorganosiloxane-polyether.

The polyether may comprise poly(ethylene oxide), poly(propylene oxide), or poly(ethylene oxide—co—propylene oxide), wherein the latter may be a statistical or block copolymer of the alkylene oxides. The polyorganosiloxane-polyether may be present as linear, branched or comb type polymers. The polymers may have a Si—O—C as well as Si—C linkages between the polysiloxane and the polyether segment. Polyorganosiloxane-polyethers are commercially available (e.g., Dow Corning® Q2-5211 (trisiloxane), Evonik's Break-Thru® S240 (trisiloxane), Momentive's Silwet L-77 and 408 (trisiloxane)).

In another aspect, the water-soluble organosilicone surfactant is a water-soluble polyether modified polysiloxane surfactant, such as a water-soluble polyether trisiloxane surfactant. In other aspects, the water-soluble organosilicone surfactant is a trisiloxane compound stable in a pH range of pH 4-9 has a static surface tension of less than 40 mN/m at 0.1% vol/vol, less than 30 mN/m at 0.1% vol/vol, less than 25 mN/m at 0.1% vol/vol, or a static surface tension of 20-30 mN/m at 0.1% vol/vol.

The amount of water-soluble organosilicone surfactant present in the compositions described herein may be any amount effective to fully dissolve the azadirachtin, terpenoids, limonoids, alkaloids and other secondary metabolites obtained from a neem extract or biomass, synthesized and/or bioengineered. For example, the amount of water-soluble organosilicone surfactant present in the compositions described herein is typically 60% to 99.9% weight based on the weight of the composition. In other aspects, the amount of azadirachtin present is from 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% weight based on the weight of the composition. In other aspects, the amount of the water-soluble organosilicone surfactant present is any range based on a combination of these percentages recited in the preceding sentence (e.g., 70%-95%, 80-97%, 82%-87%, etc.).

The compositions may include one or more additives, such as antifoam agents, compatibilizing agents, sequestering agents, neutralizing agents and buffers, and corrosion inhibitors, dyes, odorants, spreading agents, penetration aids, sticking agents, dispersing agents, thickening agents, freezing point depressants, antimicrobial agents and the like. The amount of additive(s) present in the compositions described herein is typically 0.1% to 5% weight based on the weight of the composition. In other aspects, the amount of additive(s) present is from 0.1%, 0.2%, 0.3%, 0.5%, 1%, 1.5%, 2%, 2.5%, 3%, 3.5%, 4%, 4.5%, 5%, or more weight based on the weight of the composition. In other aspects, the amount of the additive(s) present is any range based on a combination of these percentages recited in the preceding sentence (e.g., 0.1%-0.3%, 0.1%-0.5%, etc.). For example, the composition may comprise the following:

| Component | (w/w)% in Formula |
|---|---|
| Water-soluble organosilicone surfactant | 70-99.3% |
| Azadirachtin extract (15%-50% azadirachtin isomers) | 0.67-30% |
| Antifoam agent | 0-0.3% |
| | 100% |

The compositions may further include natural or synthetic active ingredients, such as insecticides, fungicides, herbicides, plant growth regulators, fertilizers, and/or micronutrients. In some aspects, such compositions comprising one or more insecticides, fungicides, herbicides, plant growth regulators, fertilizers, and/or micronutrients may be diluted to form micro-emulsions and nano-suspensions. The compositions can be mixed with natural or synthetic active ingredients (e.g., insecticides, fungicides, herbicides, plant growth regulators, fertilizers, and/or micronutrients) in, for example, a tank suitable for applying the mixture (e.g., to a field).

The compositions described herein are shelf-stable. In one aspect, at least 90% of the azadirachtin remains present after an accelerated aging test of 14 days at 54° C. in a sealed container. In other aspects, at least 91%, 92%, 93%, 94%, or 95% of the azadirachtin remains present after an accelerated aging test of 14 days at 54° C. in a sealed container. In another aspect, at least 90% of the azadirachtin remains present after storage for 12 months at ambient temperature. In other aspects, at least 91%, 92%, 93%, 94%, or 95% of the azadirachtin remains present after storage for 12 months at ambient temperature. In yet another aspect, at least 90% of the azadirachtin remains present after storage for 24 months at ambient temperature. In other aspects, at least 91%, 92%, 93%, 94%, or 95% of the azadirachtin remains present after storage for 24 months at ambient temperature.

As used herein, "chemically and physically stable" means that at least 90% of the azadirachtin remains present after an accelerated aging test of 14 days at 54° C. in a sealed container, and the components of the composition do not precipitate during storage.

As discussed herein, the compositions, before dilution, do not include a protic (or aqueous) solvent, such as water. One of skill in the art will appreciate that water may inadvertently be present in the compositions (e.g., due to moisture formation in the sealed container and not from the intentional addition of water). To the extent water exists in the compositions described here, before dilution, the compositions will have less 2%, 1%, or 0.5% by weight of water, based on the weight of the concentrate.

The compositions described herein are liquid concentrates or technical formulations typically diluted with water (or other solvent) before use. In one aspect, the compositions described herein are diluted with water at a rate of from 2.5 to 5 ml concentrate to 1 liter of water. In another aspect, the compositions described herein are diluted with water at a rate of from 3 to 4 ml concentrate to 1 liter of water. The dilution generally occurs at the site of application, and the diluted formulation is typically applied in approximately 3 days or less from the time of dilution. Compositions comprising a neem extract and/or biomass comprising azadirachtin and a water-soluble organosilicone surfactant that are diluted with water are provided herein.

The inventors have found that the diluted formulation comprises multiple components comprising a solution, micro-emulsion, and/or nano-suspension. These are advantageous formulations for delivering chemical compounds to the desired environment (e.g., crops, soil). In one aspect, particles in the diluted formulation are less than one micron. In another aspect, particles in the diluted formulation are less than 900 nm, 750 nm, or 500 nm. In other aspects, the particles are nanoparticles and thus are particles of any shape with dimensions below 500 nm (e.g., 1-100 nm) per the IUPAC's definition. See M. Vert, "Terminology for Biorelated Polymers and Applications (IUPAC Recommendations 2012)," *Pure Appl. Chem.*, Vol. 84, No. 2, pp. 377-410, 2012, which is hereby incorporated by reference.

The disclosure provides methods of making compositions described herein and diluted formulations thereof. For example, a pre-specified amount of a neem extract and/or biomass can be added to a siliconic surfactant, in a conical flask, under constant stirring until the solid is completely dissolved. Optionally, one or more additives, such as an antifoam agent, may be added and stirred thoroughly to obtain a homogeneous solution. The solution (with or without the one or more additives) is clarified by filtration through a filter medium (e.g., 10 micron) to yield the final composition. The azadirachtin content can be measured using HPLC as described, for example, in CIPAC—Collaborative International Pesticides Analytical Council: Azadirachtin A content (627/EC/M/3). 2005, England: CIPAC Methods and Publications.

The disclosure provides methods of using the compositions and diluted formulations described herein. In some aspects, the disclosure provides methods of controlling insects comprising applying any of the compositions or diluted formulations described herein to an environment of interest, such as a plant, tree, lawn or crop field. In other aspects, the methods involve organic or conventional farming by applying any of the compositions or diluted formulations described herein to an environment of interest, such as a plant, tree, lawn or crop field. These methods can be performed by spraying the compositions and/or diluted formulations using, for example, a tank mix. The compositions and diluted formulations described herein may be applied when pests are expected or when pests first appear, and as a foliar spray or a drench to soil or non-soil media to control insects.

The compositions and diluted formulations described herein may be used on agricultural crops, including, but not limited to berries (e.g., blackberry, blueberry, raspberry (black and red); bulb vegetables (e.g., garlic, leek, onion, shallot); cereal grains and grains (e.g., barley, buckwheat, corn, millet, oats, popcorn, rice, rye, sorghum (milo), wheat, wild rice); citrus fruits (e.g., citrus hybrids, grapefruit, kumquat, lemon, orange); cotton; tobacco; cucurbit vegetables (e.g., cucumber, gherkin, pumpkin, watermelon); forage crops (e.g., alfalfa); fruiting vegetables (e.g., eggplant, pepper, tomato; herbs and spices (e.g., allspice, chive, coriander, fennel lavender, pepper, thyme, vanilla); legume vegetables (e.g., bean, chickpea); leafy and brassica vegetables (e.g., arugula, broccoli, cabbage, cauliflower, kale, lettuce, spinach); miscellaneous (e.g., asparagus, avocado, banana, coffee, peanut, watercress, and all other food crops); pome fruits (e.g., apple, pear); root and tuber vegetables (e.g., artichoke, beet, carrot, potato); stone fruit (e.g., apricot, cherry, peach); tree and nut (e.g., almond, chestnut, pecan); and tropical fruit (e.g., papaya, mango, passion fruit).

The compositions and diluted formulations described herein may be used on other areas, including, but not limited to ornamental shrubs, plants, and trees; uncultivated agricultural areas (e.g., farm yards, fuel storage areas, fence rows, soil bank land, barrier strips), and general soil treatments (e.g., manure, composts, mulches, soil application with no mention of crops to be grown (potting soil, top soil)).

The compositions and diluted formulations described herein may be used against numerous pests, including, but not limited to, aphids (e.g., pea aphid, Rosy Apple Aphid), beetles (e.g., Japanese beetle), borers, (e.g., peachtree borers, peach twig borers), true bugs, (e.g., Lygus bugs, stink bugs), caterpillars, (e.g., leafrollers, cutworms, loopers, armyworms), flies (e.g., walnut husk fly, leafminers and fungus gnats), leafhoppers, leafminers, whiteflies, mealy bugs, mites, psyllids (e.g., pear psylla), weevils, scales (e.g., San Jose scale), and/or thrips, (e.g., western flower thrips).

Various embodiments will now be particularly described by way of examples. The following descriptions of specific embodiments are presented for purposes of illustration and description. They are not intended to be exhaustive of or to limit the disclosure.

EXAMPLES

Example 1—Exemplary Compositions

The inventors prepared various compositions comprising azadirachtin and a water-soluble organosilicone surfactant.

Example A

A pre-specified amount of an extracted solid neem biomass was slowly added to 82.0 g of a polyether trisiloxane surfactant (Break-Thru® S-240), in a conical flask, under constant stirring. The mixture was stirred for another 45 minutes until the solid was completely dissolved. The solution is clarified by filtration through a 10 micron filter medium to yield 99 g of the final composition. The azadirachtin content of the formulation was found to be 7.2% by weight.

Example B

A pre-specified amount of an extracted solid neem biomass was slowly added to 79.0 g of a polyether trisiloxane surfactant (Break-Thru® S-240), in a conical flask, under constant stirring. The mixture was stirred for another 45 minutes until the solid is completely dissolved. To this, 3.0 g of antifoam was added and the contents were stirred thoroughly to obtain a homogeneous solution. The solution is clarified by filtration through a 10 micron filter medium to yield 99 g of the final composition. The azadirachtin content of the formulation was found to be 7.2% by weight.

Example C

A pre-specified amount of an extracted solid neem biomass was slowly added to 83.5 g of a polyether trisiloxane surfactant (Break-Thru® S-240), in a conical flask, under constant stirring. The mixture was stirred for another 45 minutes until the solid was completely dissolved. The solution is clarified by filtration through a 10 micron filter medium to yield 99 g of the final composition. The azadirachtin content of the formulation was found to be 3.6% by weight.

Example D

A pre-specified amount of an extracted solid neem biomass was slowly added to 80.5 g of a polyether trisiloxane surfactant (Break-Thru® S-240), in a conical flask, under constant stirring. The mixture was stirred for another 45 minutes until the solid is completely dissolved. To this, 3.0 g of antifoam was added and the contents were stirred thoroughly to obtain a homogeneous solution. The solution is clarified by filtration through a 10 micron filter medium to yield 99 g of the final composition. The azadirachtin content of the formulation was found to be 3.6% by weight.

Example 2—Accelerated Storage Testing

The stability of compositions A and C in Example 1 were studied. Each of the samples were stored into a sealed glass vial and kept in an oven at 54° C. for 14 days. Analysis of azadirachtin was performed by HPLC, using UV detection at a specified wavelength and external standardization as outlined in CIPAC—Collaborative International Pesticides Analytical Council: Azadirachtin A content (627/EC/M/3). 2005, England: CIPAC Methods and Publications.

The results (below) demonstrate that the compositions are stable.

| Composition | Azadirachtin Concentration (% w/w) at T = 0 | Azadirachtin Concentration (% w/w) at T = 14 | Azadirachtin Degradation (% w/w) |
|---|---|---|---|
| A | 7.2 | 6.83 | 8.44 |
| C | 3.6 | 3.30 | 8.33 |

These results are significantly better than those presented in U.S. Pat. No. 6,811,790. For example, the '790 patent reports that, under the similar accelerated storage conditions (54° C. at 14 days), azadirachtin A in Formulations I-IV had a degradation of 68.25%, 59.60%, 35.35%, and 27.77%, respectively.

Example 3—Microemulsions

Figure 1B:
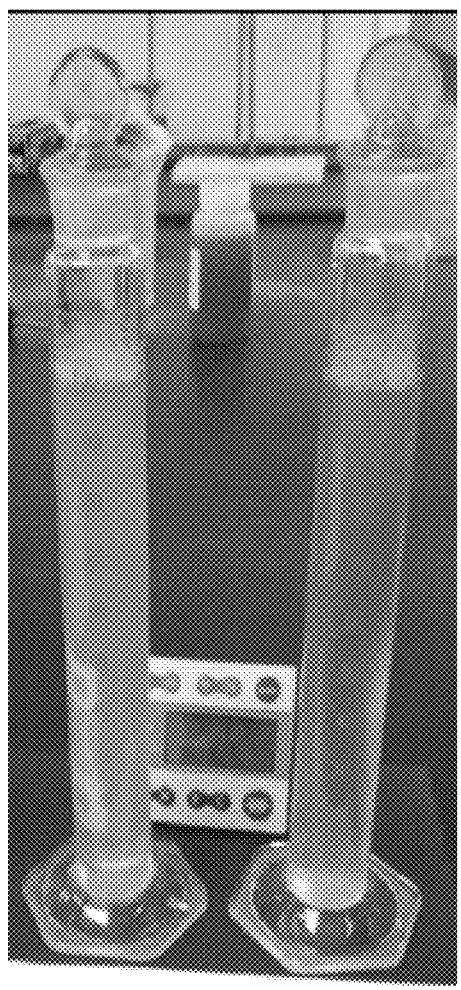
Figure 1C:

Microemulsions of compositions A and C were prepared by diluting sufficient formulated product in standard hard water (342 ppm) to provide 0.024 grams of total azadirachtin content. Then, each measuring cylinder is inverted in a rate of 30 times per minute, and the liquid contents are uniformly mixed. Then the cylinders are allowed to stand. See CIPAC MT 36.3. The diluted product is observed visually for initial performance and emulsion stability at 2 and ~22 hours for separation and/or creaming and, if observed, the degree measured. The results are shown in FIGS. 1A-1C, which show no separation or creaming at ~22 hours.

The microemulsions are typically applied in amounts sufficient to deliver from about 0.006 to 0.02 kg a.i./acre.

The invention claimed is:

1. A composition comprising a neem extract or biomass comprising azadirachtin and a water-soluble, non-ionic polysiloxane surfactant, wherein at least 90% of the azadirachtin remains present after an accelerated aging test of 14 days at 54° C. in a sealed container, and wherein the composition is a non-aqueous, liquid concentrate.

2. The composition of claim 1, wherein the neem extract or biomass comprises azadirachtin A and azadirachtin B.

3. The composition of claim 1, wherein the neem extract or biomass comprises terpenoids, limonoids, and alkaloids.

4. The composition of claim 1, wherein the water-soluble, non-ionic polysiloxane surfactant is a water-soluble polyether modified polysiloxane surfactant.

5. The composition claim 1, wherein the water-soluble, non-ionic polysiloxane surfactant is a trisiloxane compound stable in a pH range of pH 4-9 has a static surface tension of less than 40 mN/m at 0.1% vol/vol.

6. The composition of claim 5, wherein the trisiloxane compound has a static surface tension of less than 30 mN/m at 0.1% vol/vol.

7. The composition of claim 5, wherein the trisiloxane compound has a static surface tension of less than 25 mN/m at 0.1% vol/vol.

8. The composition of claim 1, wherein the concentration of azadirachtin is 0.1-10% weight/weight of the composition.

9. The composition of claim 1, further comprising one or more natural or synthetic insecticides, fungicides, herbicides, plant growth regulators, fertilizers, and/or micronutrients.

10. The composition claim 1, wherein said composition is capable, upon dilution, of providing a solution, microemulsion, and/or nano-suspension.

11. A composition comprising
a formulation comprising a neem extract or biomass comprising azadirachtin and a water-soluble organosilicone surfactant, wherein at least 90% of the azadirachtin remains present after an accelerated aging test of 14 days at 54° C. in a sealed container, and wherein the formulation is a non-aqueous, liquid concentrate, and
water,
wherein azadirachtin is present as particles less than one micron.

12. The composition of claim 11, wherein the particles are less than 500 nm.

13. A method controlling insects comprising applying the composition of claim 11 to a plant, crop, field, and/or soil.

14. A method for organic or conventional farming comprising applying the composition of claim 11 to a plant, crop, field, and/or soil.

15. The method of claim 13, further comprising spraying the composition to said plant, crop, field, and/or soil.

16. A method of making a composition, comprising
diluting a formulation comprising a neem extract or biomass comprising azadirachtin and a water-soluble no non-ionic polysiloxane surfactant, wherein at least 90% of the azadirachtin remains present after an accelerated aging test of 14 days at 54° C. in a sealed container, and wherein the formulation is a non-aqueous, liquid concentrate with water.

17. A composition comprising
a formulation comprising a neem extract or biomass comprising azadirachtin and a water-soluble organosilicone surfactant, wherein at least 90% of the azadirachtin remains present after an accelerated aging test of 14 days at 54° C. in a sealed container, and wherein the formulation is a non-aqueous, liquid concentrate, and
water,
wherein the composition is a micro-emulsion comprising azadirachtin and a water-soluble organosilicone surfactant, wherein the concentration of azadirachtin is 0.1-10% A weight/weight of the composition.

18. A composition comprising
a formulation comprising a neem extract or biomass comprising azadirachtin and a water-soluble organosilicone surfactant, wherein at least 90% of the azadirachtin remains present after an accelerated aging test of 14 days at 54° C. in a sealed container, and wherein the formulation is a non-aqueous, liquid concentrate, and
water
wherein the composition is a nano-suspension comprising azadirachtin and a water-soluble organosilicone surfactant, wherein the concentration of azadirachtin is 0.1-10% weight/weight of the composition.

19. The composition of claim 1, wherein the concentration of azadirachtin is 3-4% weight/weight of the composition.

20. The composition of claim 1, wherein the concentration of azadirachtin is 7-8% weight/weight of the composition.

21. The composition of claim 11, further comprising one or more natural or synthetic active ingredients.

22. The composition of claim 21, wherein the one or more natural or synthetic active ingredients comprise an insecticide, a fungicide, an herbicide, a plant growth regulator, a fertilizer, and/or a micronutrient.

23. A composition comprising a formulation comprising a neem extract or biomass comprising azadirachtin and a water-soluble non-ionic polysiloxane, wherein at least 90% of the azadirachtin remains present after an accelerated aging test of 14 days at 54° C. in a sealed container, and wherein the formulation is a non-aqueous, liquid concentrate, and
water.

24. The composition of claim 23, wherein the water-soluble organosilicone surfactant is a water-soluble polyether modified polysiloxane surfactant.

25. The composition claim 23, wherein the water-soluble organosilicone surfactant is a trisiloxane compound stable in a pH range of pH 4-9 has a static surface tension of less than 40 mN/m at 0.1% vol/vol.

* * * * *